United States Patent [19]
Katoot

[11] Patent Number: 5,932,299
[45] Date of Patent: Aug. 3, 1999

[54] METHOD FOR MODIFYING THE SURFACE OF AN OBJECT

[76] Inventor: Mohammad W. Katoot, 1080 Laurian Park Dr., Roswell, Ga. 30075

[21] Appl. No.: 08/837,791

[22] Filed: Apr. 22, 1997

Related U.S. Application Data

[63] Continuation-in-part of application No. 08/679,685, Jul. 11, 1996, abandoned, and application No. 08/636,427, Apr. 23, 1996, abandoned

[60] Provisional application No. 60/028,148, Oct. 10, 1996, and provisional application No. 60/045,643, Apr. 18, 1997.

[51] Int. Cl.⁶ ....................................................... C08F 2/48
[52] U.S. Cl. ...................... 427/508; 427/385.5; 427/512; 427/521; 427/557; 427/559; 427/595
[58] Field of Search .................................. 427/508, 512, 427/521, 557, 559, 595, 385.5

[56] References Cited

U.S. PATENT DOCUMENTS

| | | |
|---|---|---|
| 3,016,599 | 1/1962 | Perry, Jr. . |
| 3,341,394 | 9/1967 | Kinney . |
| 3,655,862 | 4/1972 | Dorschner et al. . |
| 3,692,618 | 9/1972 | Dorschner et al. . |
| 3,704,198 | 11/1972 | Prentice . |
| 3,705,068 | 12/1972 | Dobo et al. . |
| 3,755,527 | 8/1973 | Keller et al. . |
| 3,802,817 | 4/1974 | Matsuki et al. . |
| 3,849,241 | 11/1974 | Butin et al. . |
| 3,853,651 | 12/1974 | Porte . |
| 3,978,185 | 8/1976 | Butin et al. . |
| 4,064,605 | 12/1977 | Akiyama et al. . |
| 4,091,140 | 5/1978 | Harmon . |
| 4,100,319 | 7/1978 | Schwartz . |
| 4,100,324 | 7/1978 | Anderson et al. . |
| 4,118,531 | 10/1978 | Hauser . |
| 4,340,563 | 7/1982 | Appel et al. . |
| 4,405,297 | 9/1983 | Appel et al. . |
| 4,434,204 | 2/1984 | Hartman et al. . |
| 4,627,811 | 12/1986 | Greiser et al. . |
| 4,644,045 | 2/1987 | Fowells . |
| 4,663,220 | 5/1987 | Wisneski et al. . |
| 5,232,748 | 8/1993 | Horowitz et al. . |

FOREIGN PATENT DOCUMENTS

| | | |
|---|---|---|
| 0 469 117 A2 | 12/1991 | European Pat. Off. . |
| 0 597 510 A1 | 9/1993 | European Pat. Off. . |
| 912 280 | 12/1962 | United Kingdom . |
| WO 92/07464 | 5/1992 | WIPO . |
| WO 95/05408 | 2/1995 | WIPO . |

OTHER PUBLICATIONS

Wenta et al., "Manufacture of Superfine Organic Fibers," Navy Research Laboratory, Washington, D.C., NRL Report 4364 (111437), May 25, 1954, United States Department of Commerce, Official of Technical Services.

Wenta, et al., "Superfine Thermoplastic Fibers," *Industrial and Engineering Chemistry*, vol. 48, No. 8, pp. 1342–1346 (1956); (No Match Avail.).

Butin, et al., "Meltblowing–A One Step Web Process for New Non–Woven Products," *Journal of the Technical Association of the Pulp and Paper Industry*, vol. 56, No. 4, pp. 74–77 (1973) (No Month Avail.).

*Primary Examiner*—Bernard Pianalto
*Attorney, Agent, or Firm*—Jones & Askew LLP

[57] ABSTRACT

The present invention relates to several novel compositions and methods employing infrared radiation, microwave radiation or high voltage polymerization for modifying the surfaces of materials to impart desired characteristics thereto. More particularly, the present invention relates to a method for modifying the surfaces of objects to increase the lubricity, hydrophilicity, hydrophobicity, or biofunctionality of the surface of the object.

26 Claims, No Drawings

METHOD FOR MODIFYING THE SURFACE OF AN OBJECT

CROSS REFERENCE TO RELATED APPLICATIONS

The present application is a continuation-in-part of U.S. application Ser. No. 08/679,685 filed on Jul. 11, 1996, and U.S. application Ser. No. 08/636,427 filed on Apr. 23, 1996, both now abandoned. The present application also claims priority to U.S. Provisional Application Ser. No. 60/028,148 filed Oct. 10, 1996, and U.S. Provisional Application filed Apr. 18, 1997, Ser. No. 60/045,643.

TECHNICAL FIELD

The present invention relates to a compositions and methods for modifying the surfaces of materials to impart desired characteristics thereto. More particularly, the present invention relates to a method for modifying the surfaces of objects to increase the hydrophilicity, hydrophobicity or biofunctionality of the surface.

BACKGROUND OF THE INVENTION

The surface properties of objects greatly influence their interaction with the atmosphere, gases, fluids and with biological systems. The relative hydrophobicity and hydrophilicity of a surface significantly affect physical, chemical and biological properties including, but not limited to, friction, wetability, oxidation, interaction with proteins and other molecules, antigenicity and biocompatability.

Millions of surgical procedures are performed each year which require direct contact between living tissues and various surgical instruments, medical devices and prosthetic implants constructed of plastics, polymers, metals such as stainless steel, or materials made from composites of these materials. Despite the many positive benefits which are gained by the use of polymeric compounds for these purposes, there are often serious complications. Plastic and elastomeric, rubbery polymers are generally hydrophobic by nature which means these materials tend to repel, rather than absorb, water. As a result, dynamic contact between the non-water absorbing polymer surfaces and human fluid-based tissues, including blood, can cause significant abrasive damage to fragile and sensitive human cells and tissues. These dynamic contacts can also cause a wide range of undesirable effects such as tissue and cell adhesion, inflammation, thrombogenicity (clotting of the blood), hemolysis, bacterial adhesion and infections, unwanted mineral deposits, and increased pain or limited motion for joint and tendon prostheses.

Materials and fabrics used in the manufacture of clothing, diapers, sanitary napkins, sheets, bedding, sails, furniture, rugs, drapes, car seats and the like are often treated to enhance some property such as hydrophilicity, hydrophobicity or biological reactivity. However, many of the current methods of coating such objects offer only temporary protection and repeated application of protective sprays is often necessary. In addition, many materials have proven especially difficult to modify, decreasing their utility in specific applications such as the manufacture of certain items of clothing or absorbent materials. For example, many have attempted unsuccessfully to modify the surface properties of polypropylene. What is needed is a composition and method to modify materials and fabrics to achieve the desired surface properties.

Exposure of metallic surfaces to solvents such as water, saline and other chemicals may cause chemical oxidation and pitting or wasting of the surface thereby reducing its tensile strength. Oxidative changes also change the surface properties of metals and increase friction with air, liquid and solids. For example, the maritime industry expends vast sums to protect and maintain the outer hulls of ships and other metallic components against the degradative effects of oxidation. Ships with increased surface oxidation of their metallic skins display increased friction with water and air, gradually becoming less efficient. Similar problems affect the aviation, automobile and railroad industries. In addition to the damaging effects of oxidation on the metallic skins of transportation vehicles, the smoothness of their surfaces affects friction and therefore the efficiency and speed. What is needed is a special coating that would enable ships to travel through water with decreased friction, thereby increasing speed and efficiency. Other types of motor vehicles such as automobiles, trucks, and airplanes would become more efficient with a friction reducing coating.

Steel structures such as bridges, buildings, water towers, silos and automobiles also require continual maintenance to protect against the ravages of oxidation induced by air, water, salt and numerous pollutants such as sulfuric acid. What is needed is a composition and method of treating metallic surfaces at the time of their manufacture and also after their incorporation into a product or structure in order to protect the surfaces. What is also needed is a method and composition to maintain structures in order to minimize new and existing oxidation.

Modification of the surface of an object can change the hydrophobic and hydrophilic properties of the surface and may affect physical, chemical and biological properties. Materials may be applied to the surface of objects through various chemical and physical means. The surfaces of objects made of polymers, plastics, metals, ceramics and composite materials have all been modified. One approach involves grafting material onto the surface through the use of gamma ray irradiation which requires special radiation facilities and costly gamma ray sources. In addition to these financial considerations, use of gamma radiation is potentially dangerous to workers exposed to gamma rays during surface modification procedures. Workers using gamma radiation must be monitored routinely for exposure levels to different regions of the body. In addition, special coating applications such as coating the surfaces of large objects may not be amenable to the gamma ray grafting process. Finally, certain types of materials have not been successfully modified due to lack of understanding the relevant parameters or due to competing reactions.

Accordingly, what is needed is a less expensive method of grafting materials onto the surface of objects which does not require special radiation facilities and costly gamma ray sources. What is also needed is a method which does not pose the radiation safety risks inherent in the use of gamma radiation. A method is also needed which is rapid and permits coating of special objects which cannot be coated with conventional processes, and a method which allows great flexibility in the various aspects of the modification relevant to both materials and surfaces.

What is needed is an inexpensive and rapid method of treating the surfaces of devices including, but not limited to, surgical instruments, medical devices, implants, prostheses, and hematology equipment so that the surface tension of the device is reduced thereby decreasing the trauma caused by the device on living tissue and cells.

What is also needed is an inexpensive and rapid method of treating surfaces of materials to be used in the construction of various objects including, but not limited to, buildings, bridges, silos, ships, and motor vehicles such as airplanes, trucks and automobiles, to prevent and retard oxidation. What is also needed is a treatment which will modify the hydrophobic and hydrophilic properties of the surfaces of objects used in the transportation industry to decrease the surface friction. This treatment method should also be amenable to application for routine maintenance of surfaces and for modifying their surface properties.

SUMMARY OF THE INVENTION

The present invention addresses problems described above by providing compositions and simple, inexpensive, rapid and effective methods for treating the surface of an object using infrared radiation, microwave radiation, or high voltage polymerization. These compositions and methods are effective in altering the surface properties of the treated objects to produce desired properties.

The present invention includes several novel compositions called micrograft initiators that can be used with a wide variety of monomers, oligomers or polymers to graft the monomer, oligomer or polymer to the surface of the object thereby imparting the physical properties of the monomer, oligomer or polymer to the surface of the object. In this way, the surface of the object can be made lubricious, hydrophilic or hydrophobic depending upon the physical properties of the monomer, oligomer or polymer. These grafts are also called micrografts. The micrograft initiators of the present invention are designed for use with infrared radiation, microwave radiation, or high voltage polymerization. Other molecules and compounds may be used in the present invention to impart lubricious, hydrophilic, hydrophobic and other properties to the treated surfaces. The present invention avoids the use of gamma radiation and the inherent costs and health safety risks. The method of the present invention is extremely rapid and can also be used to coat irregular and large surfaces on production lines. Furthermore, the present invention may be employed to modify the surfaces of objects after their manufacture and use, thereby maintaining the surface, modifying its surface properties, and decreasing oxidation and corrosion.

The present invention may be used to coat surfaces and make them more lubricious, hydrophilic or hydrophobic depending upon the desired physical property. The present invention may also be used to incorporate molecules and other compounds into or onto the surface of objects which impart biofunctional properties to the surface of the object.

In one embodiment the present invention may be used to treat a device so that the treated surface has an extremely low surface tension. The present invention can be used to treat the surfaces of a wide variety of materials including plastics, polymers, ceramics, metals and composite materials. In one embodiment, the device modified with the present invention can be implanted into living tissue with a minimum of side effects. For example, a vascular stent can be treated according to the present invention to increase the hydrophilicity of the interior surface of the stent or to add phospholipids or other biofunctional molecules to the exterior surface of the stent. This stent may also be modified to contain drugs and anticoagulation agents (heparin, warfarin, etc.) to minimize clotting near damaged tissues and reduce the risk of bleeding elsewhere. This stent may be implanted into a blood vessel. While not wanting to be bound by this hypothesis, it is believed that the treated vascular stent causes a minimum of thrombogenic events due to decreased platelet adherence when compared to untreated vascular stents. Thus, the present invention provides a unique method for producing permanent tissue protective surface modifications on polymeric, metallic, ceramic and composite materials. The present invention improves many prior art medical devices by minimizing damage and harmful side effects resulting from detrimental tissue and cell interactions with surfaces, and reduces tissue trauma and infections caused by surface adhesions inherent in most plastics, polymers and metals.

The surface modification technology of the present invention involves a novel process for chemically grafting hydrophilic polymers to a wide variety of base polymers using novel microwave initiated materials and microwave radiation, novel infrared initiated materials and infrared radiation, or high voltage polymerization (plasma fusion technology) to affect the grafting of the materials to the surface. The resulting chemically bound surface may be uniform, endurable and hydrophilic (water absorbing), hydrophobic, and/or bioactive.

In one embodiment of the present invention, coated medical instruments and devices are smooth, lubricious, and nonadherent to cells and tissues. In this embodiment of the present invention, coated medical instruments and devices exhibit reduced abrasion and friction with sensitive bodily tissues such as blood cells, vascular endothelium, peritoneum, pericardium, and the fragile surfaces of the respiratory system including tissues such as the lining of the trachea, the urinary system including the urethra and ureter, the gastrointestinal system, and the cardiovascular system, thereby minimizing tissue damage and potentially associated, life-threatening problems. In addition, surfaces modified according to the present invention are less likely to promote the occurrence of infectious bacteria and other harmful microorganisms which cause post-operative blood clotting, infection, and infection-related complications.

The present invention also provides methods and compositions for treating surfaces of fabrics and papers. After treatment according to the present invention, the surface of the fabric or paper is highly wettable. This has great utility where wetability of the surface of the fabric or paper is advantageous. Such uses include, but are not limited to, towels, washcloths, gauze pads, bandages, surgical towels, surgical drapes, diapers, incontinence devices and clothing, sanitary napkins, paper napkins, bed sheets, the interior of surgical uniforms and scrubs, the interior of many types of clothing, and the like.

In another embodiment, the present invention also provides a method and composition for treating surfaces to increase their hydrophobicity. Surfaces with increased hydrophobicity are useful on objects, especially metal objects, that are damaged by exposure to water, to salt water or to other solutions containing chemicals such as oxidizing and caustic chemicals, including, but not limited to, sulfuric acid, phosphoric acid, nitric acid, potassium hydroxide and sodium hydroxide. By increasing the hydrophobic and anticorrosive properties of such surfaces, the costs and labor associated with maintenance of these surfaces are reduced. For example, treatment of the surfaces according to the present invention of a ship exposed to salt water or to other damaging pollutants in salt or fresh water, such as those pollutants that cause oxidation of metals, decreases oxidation of the metal. A ship hull surface treated in this manner also exhibits increased speed due to decreased friction with water. A ship's hull can also be treated according to the present invention to prevent the adherence of barnacles.

In another embodiment of the present invention, use of the present invention to treat metal used in vehicles such as motor vehicles, airplanes, trains, and bicycles decreases oxidation of these vehicles. Treatment of steel girders or other metals used in the construction industry prolongs the useful life of these materials by decreasing the oxidizing effects of chemicals in the air or in water, such as the oxidizing effects of sulfuric acid and other pollutants in acid rain. The present invention may be used to treat materials used in construction as well as existing structures such as bridges, tunnels, water towers, communication transmission towers, power line towers, and silos, thereby decreasing costly maintenance.

Another embodiment of the present invention is the treatment of fabrics and papers to increase their hydrophobicity. For example, clothing designed for outerware, such as raingear, more efficiently repels water after treatment according to the present invention. The present invention may also be used to treat rugs, drapes, furniture, and motor vehicle upholstery to increase repellence. The outer surfaces of surgical gowns and other forms of medical clothing that repel blood, urine and other biological fluids provide increased protection for physicians, nurses and other health care providers by decreasing transmission of infection and disease such as human immunodeficiency virus (HIV), hepatitis, meningitis, tuberculosis and bacterial infections, through reduced contact with biological fluids.

Modification of the surfaces of protective clothing and gloves according to the present invention to more effectively repel biological fluids and chemicals provides increased protection for clinical laboratory personnel and others in basic and clinical research involving biological fluids and chemicals. Such surface modification of clothing and gloves is useful to morticians, medical examiners, pathologists, histologists, anatomists and students such as medical and veterinary students. Surface modification of protective clothing of employees who utilize harmful substances such as in the chemical, petroleum and nuclear industries provides enhanced protection to these individuals.

The present invention also provides the means to modify the inner and outer layers of clothing to provide, for example, a hydrophilic interior and a hydrophobic exterior, thereby permitting perspiration to be absorbed while retarding or preventing the transmission of chemicals or biological agents from outside the garment. Clothing modified in this manner is useful in the medical industry, as well as the chemical, petroleum, nuclear, and fire-fighting industries.

Other fabrics and materials that may be treated with the present invention include canvas and materials used in the manufacture of outerware including jackets, parkas, vests, overcoats, hats, gloves, ski apparel, sails, tents, shoes, jogging shoes, boots, automobile convertible tops and camping gear where water repellency is advantageous. Special materials such as GORETEX® may also be treated. Wood used in the construction of decks, floors, walls, paneling, roofs, trim, fascia board, window frames, shingles boats, including sailboats and rowboats may also be treated with the compositions and methods of the present invention to protect their surfaces and decrease the need for frequent maintenance and application of solvents, waxes, oils, water repellent compounds, paints and stains.

The present invention may also be used to modify the biofunctional properties of a surface. Incorporation of certain molecules or compounds into the surface coating of an object may alter the biological properties of the surface. Such molecules and compounds include, but are not limited to, proteins, enzymes, enzyme inhibitors, immunological molecules, anti-coagulation compounds, anti-inflammatory compounds, hormones, neurotransmitters, peptides, lipids, nucleic acids, sugars, carbohydrates, glycoproteins, lectins, bacteria, viruses, replication inhibitors, proteases, antibiotics, antifungals, bacteriostatic compounds, toxins, microbials, anti-microbials, growth factors, angiogenic factors, nutrients, and vitamins. For example, incorporation of specific molecules into the surface of an object might impart to the object the property of attracting certain kinds of cells or molecules to the coated surface. Molecules or combinations of molecules incorporated into the surface of an object might also stimulate a biological reaction surrounding the material, for example, in promotion of scab formation to close a wound. A biocompatible implant coated with angiogenic factors might increase the vascularity of the region surrounding the implant to promote perfusion and healing. A stent coated on its interior surface with a hydrophilic coating to reduce thrombogenic properties might also be coated on its exterior surface with molecules that promote growth of endothelial cells. In another embodiment of the present invention, a surface modified implant coated with specific molecules or combinations of molecules such as receptors or antibodies might retard the immunorejection process by binding molecules that would normally bind to a non-modified implant and initiate a series of events leading to rejection of the implant. A prosthetic implant, for example an artificial knee or component thereof, coated with molecules derived from connective tissue or synovial cells might exhibit decreased rejection compared to the non-coated prosthetic implant. Surgical gloves treated with anti-viral agents might decrease the transmission of disease including, but not limited to, HIV and hepatitis.

Accordingly, an object of the present invention is to provide compositions and methods to modify the physical, chemical or biological properties of surfaces.

Another object of the present invention is provide compositions and methods employing infrared radiation or microwave radiation to modify the properties of surfaces.

A further object of the present invention is to provide compositions and methods to modify the properties of surfaces of objects made from polymers, ceramics, metals, wood, fabrics or materials and composites thereof.

Accordingly, it is an object of the present invention to provide compositions and methods for treating the surface of a polymer, ceramic, metallic, wooden, fabric or composite device thereby making the surface hydrophilic.

Another object of the present invention to provide materials, methods, and compositions for treating the surface of fabric thereby making the fabric hydrophilic and highly wettable.

Another object of the present invention is to provide compositions and methods for treating the surface of a polymer, ceramic, metallic, wooden, fabric or composite device thereby making the surface hydrophobic. An additional feature of these treated hydrophobic surfaces is that they display decreased friction in water and air.

Another object of the present invention is to provide a treatment for floors to increase their surface hydrophobic properties and reduce the need for frequent application of maintenance solutions such as paint, stains, varnish and wax.

It is yet another object of the present invention to provide methods and compositions for treating the surface of fabric thereby making the fabric more hydrophobic and less wettable.

Another object of the present invention is to make sanitary napkins, diapers and hospital bedding or materials used in their manufacture more hydrophilic and wettable.

Another object of the present invention is to provide compositions and methods of coating the surfaces of devices and objects which decreases adhesion of cells, especially platelets and smooth muscle cells.

It is another object of the present invention to provide compositions and methods of coating the surfaces of devices which may be implanted into or used in biological organisms, such devices including, but not limited to, stents, guide wires, catheters, grafts, balloons, sutures, screws, staples, pins, plates, drainage devices, shunts, tubes, gastrointestinal tubes including but not limited to nasogastric tubes, gastric tubes, and jejunal tubes, and endoscopy devices, vascular tubes and shunts, tubes for placement in the respiratory system including endotracheal tubes, tubes to drain the middle ear, drainage tubes for wounds or for fluids in the body cavities including the peritoneal, pleural, cranial, and pericardial cavities, tubes for placement in the urinary system, especially within the urethra, bladder and ureter, tubes for placement in the reproductive system, especially the vas deferens, vagina, uterus, and ovarian tubes, tubes for placement in the cardiovascular system, tubes which act as shunts such as tubes connected to the cerebroventricular system, cuffs, pumps, minipumps, electrodes, prosthetic devices, artificial joints, artificial lenses, contact lenses and implants. Implants include but are not limited to artificial knees, ankles, hips, shoulders, thyroplastic and laryngoplastic devices, pumps, tubes, lens implants, and electrodes. A specific feature of these coated implants is that they exhibit improved biocompatability. Another specific feature of these coated devices is that they exhibit increased lubricity.

Another object of the present invention is to provide compositions and methods for treating the surface of vascular stents which minimize or prevent thrombogenic activity caused by the vascular stent.

It is yet another object of the present invention to provide methods and compositions for treating the surface of instruments and prosthetic devices. An advantage of the present invention is that these treated surfaces possess improved biocompatability properties.

Another object of the present invention is to provide compositions and methods of modifying the properties of surfaces to make the surfaces biofunctional. A specific advantage of the present invention is that the biofunctionality of these surfaces may be engineered to produce a specific biological response.

These and other objects, features and advantages of the present invention will become apparent from the following detailed description, when taken in conjunction with the claims.

DETAILED DESCRIPTION OF THE INVENTION

The present invention provides novel compositions and methods employing infrared radiation, microwave radiation or high voltage polymerization for modifying the surfaces of objects to impart desired characteristics thereto. More particularly, the present invention provides a method for modifying the surfaces of objects to increase the lubricity, hydrophilicity, hydrophobicity and/or biofunctionality of the surface. Various materials, such as plastics, polymers, ceramics, metals, wood, natural and synthetic fibers, woven or nonwoven webs or composite materials may be treated with the composition and method of the present invention. Accordingly a variety of objects comprised of these materials and fibers may be treated to modify their surface properties.

In one embodiment, the present invention provides methods and compositions for treating the surface of objects so that the resulting treated surface is hydrophilic and exhibits a very low surface tension. In practicing the present invention, surface to be treated is coated with a unique polymer composition and is then exposed to infrared radiation. In another embodiment, the surface to be treated is coated with a unique polymer composition and is then exposed to microwave radiation. The method of the present invention substantially irreversibly binds the polymer to the surface of the object and reduces the surface tension of the surface to water and greatly increases the hydrophilic properties of the surface.

The hydrophilic graft polymer surface modifications of the present invention are advantageous for intraocular lens implants (anterior chamber, posterior chamber or phakic), but are also of great value in affording improved tissue protection and improved biocompatibility for other implants such as corneal inlays, kerato-prostheses, vascular stents, epikeratophalia devices, glaucoma shunts, retinal staples, scleral buckles, dental prostheses, thyroplastic devices, laryngoplastic devices, etc.

Plastic and metallic surgical instruments and implements including, but not limited to, probes, retractors, tissue and vessel separators, irrigation and aspiration tools, phacoemulsification tools, sponges, hemostats, clamps, blades including scalpel blades, gloves, lens glides, positioning tools, catheters, forceps, insertion tools, staples, sutures, etc., may be treated to afford tissue protective surface qualities in accordance with the present invention. Surgical instruments and implements constructed from polymers, metals, or composite materials and including those named above may also be surface modified using the composition and method of the present invention.

Medical devices, such as hard and soft contact lenses, stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, blood tubing may also be beneficially treated in accordance with the method of the present invention. Many of these devices may be made more lubricious when treated in accordance with the method of the present invention.

Implants which may be modified according to the present invention include, but are not limited to, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves.

Modification of these instruments, devices, implants, etc., improves the surfaces thereof so as to improve blood compatibility and reduce tissue adhesion and tissue damage during surgical contact and manipulation. Moreover, the present invention reduces cell adhesion for reduced inflammation, reduces fibrous capsule formation for soft tissue implants, and reduces thrombogenicity for cardiovascular devices and prostheses. The present invention also decreases bacterial adhesion, thereby reducing the incidence of infection. The present invention also reduces interfacial abrasion and friction which is of special value for joint and tendon prostheses.

Polyolefins and polyolefin/hydrocarbon block polymers are useful for constructing medical tubing, catheters, blood bags, sutures, etc. Copolymers may be thermoplastic elastomers which combine rubbery properties with extrudable or injection moldable processing properties. Surface modification of such materials according to the present invention is effective in changing the normal surface characteristics for these polymers from hydrophobic to hydrophilic.

The fluorocarbon polymers are widely used for catheters (i.e., intravenous catheters), for vascular prostheses (i.e., vascular grafts), and for coating medical devices, instruments and implants due to their biocompatibility and inertness. However, the surface properties may be improved significantly according to the present invention to reduce cell and tissue adhesion and improve blood compatibility.

The silicone polymers are widely used for medical tubing and catheters for mammary implants and other soft tissue prostheses. Hydrophilic surface modification, according to the present invention, reduces cell and tissue abrasion and adhesion and also fibrous capsule formation which is a major complication of soft tissue implants. Silicone polymers may be made more lubricious with the surface treatment of the present invention. Similarly, polyvinyl chloride surface modification to produce more hydrophilic vinyl tubings and film surfaces can reduce thrombogenicity and improve biocompatibility of blood tubing, blood bags, catheters, and other medical devices made of materials such as polyvinyl chloride, SILASTIC® (Dow Chemical Co.), polypropylene, polystyrene, and polycarbonate.

Polyurethanes, which are used for such applications as pacer leads, intravenous catheters, enteral feeding tubes, vascular grafts, etc., are also beneficially modified by the process of materials of the present invention to produce more hydrophilic surfaces and make such devices more biocompatible.

Each of the above-described process conditions and parameters of the method of the present invention may be varied without undue experimentation to produce certain specific combinations which are particularly advantageous for the surface modification of particular materials or combinations of materials.

Typical metallic surfaces which may be treated according to the method of the present invention include, but are not limited to, iron and iron alloys including various alloy steels, stainless steel, nickel, copper, cobalt, and a wide variety of metallic alloys.

Suitable polymeric substrates include, but are not limited to, polyacrylates and methacrylates (i.e., polymethylmethacrylate, polymethylacrylate, polybutylmethacrylate, etc.); polyolefins (polyethylene, polypropylene, polybutadiene), styrene-butadiene copolymers, ethylene propylene copolymers, styrene-ethylene/butadiene/styrene block copolymers, polycarbonates, fluorocarbon polymers (i.e., polyvinylidene fluoride-PVDF, polytetrafluoroethylene (PTFE), polyperfluoroethylenepropylene-FEP, polysiloxanes, various aliphatic and aromatic polyurethanes, including polyurethane polyester or polyether block copolymers, polyvinyl chloride, various polyesters including polyethylene terephthalate (PET), polycarbonate/polydimethylsiloxane copolymers, and the like.

Inorganic glasses and ceramics of various compositions such as silica, soda glass, borosilicate glass, high calcium and phosphate glasses, quartz, etc., may be utilized according to the present invention.

The surface modification treatment of the present invention is also especially well suited for treating surfaces of fabrics and paper products. The present invention will impart high wetability characteristics to the fabric or paper product, making the fabric or paper product especially well suited for any application which requires extreme wetability of the vinyl, polypropylene or PTFE product in accordance with the present invention.

In those embodiments in which the article is a non-woven web, such non-woven web, in general, can be prepared by any of the means known to those having ordinary skill in the art. For example, the non-woven web can be prepared by such processes as melt blowing, conforming, spunbonding, hydroentangling, carding, air laying, and wet forming.

The non-woven web more typically will be a non-woven web prepared by melt blowing, coforming, spunbounding, and the like. By way of illustration only, such processes are exemplified by the following references which are incorporated herein by reference in their entirety. See, for example, U.S. Pat. No. 3,016,599; U.S. Pat. No. 3,704,198; U.S. Pat. No. 3,755,527; U.S. Pat. No. 3,849,241; U.S. Pat. No. 3,978,185; and U.S. Pat. No. 4,663,220. See also, Wenta, "Superfine Thermoplastic Fibers," Industrial and Engineering Chemistry, Vol. 48, No. 8, pp. 1342–1346 (1956); Wenta et al., "Manufacturer of Superfine Organic Fibers," Navy Research Laboratory, Washington, D.C., NRL Report 4364 (111437), May 25, 1954, United States Department of Commerce, Official of Technical Services; and Butin et al. "Meltblowing-A One Step Web Process For New Non-Woven Products," Journal of the Technical Association of the Pulp and Paper Industry, Vol. 56, No. 4, pp. 74–77 (1973). Conforming references include U.S. Pat. Nos. 4,100, 324, and 4,118,531. Spunbounding references include U.S. Pat. Nos. 3,341,394; 3,655,862; 3,692,618; 3,705,068; 3,802,817; 3,853,651; 4,064,605; 4,091,140; 4,100,319; 4,340,563; 4,405,297; 4,434,204; 4,627,811; and 4,644,045.

The term "hydrophobic polymer" is used herein to mean any polymer resistant to wetting, or not readily wet, by water, that is having a lack of affinity for water. A hydrophobic polymer typically will have a surface-free energy of about 40 dynes per centimeter ($10^{-5}$ newtons per centimeter or less.) Examples of hydrophobic polymers include, but are not limited to, polyolefins, such as polyethylene, isobutene, methacrylates, halogenated polymers, fluorinated polymers, styrene polymers, etc.

The term "hydrophilic polymer" is used herein to mean any polymer that promotes wetting by water of a surface. Examples of hydrophilic polymers include, but are not limited to, hydroxyethyl methacrylate, N-vinyl pyrollidone, carboxymethyl cellulose, acrylamide, polyethylene glycol, hydroxypropyl acrylamide, sulfopropyl acrylate, styrene sulfonic acid, potassium styrene sulfonic propyl acrylate, methacrylamide, acrylate, acrylic acid, methacrylic acid, and proteins, such as heparin.

The term "grafting" is employed to mean the incorporation of the composition of the present invention onto and into a surface. The term "micrograft" is used synonomously with the term "graft" to indicate the graft of the selected compound or compounds onto and into the surface to be treated using the compositions and methods of the present invention. The term "hydrophilic" literally means water loving or the wetability of a surface. By the term "hydrophobic" is meant ability to repel water. The term "microwave" means radiation in the range of approximately 1 MHz to 20 GHz. The term "infrared" means radiation in the range of approximately 1 to 12 μm in wavelength. The term "high voltage polymerization" as used herein means application of high amounts of voltage to achieve polymerization and grafting of the desired materials onto the chosen surface.

The present invention also includes the incorporation of biofunctional compounds into the surface of an object to impart biological properties to the surface of the object. Biological properties refer to biological activity of a treated surface in a biological system. A treated object may become more or less active in a biological system after treatment of the surface than it was before the treatment of the surface. The term "biofunctional compound" includes, but is not limited to, proteins, enzymes, enzyme inhibitors, immunological molecules, hormones, neurotransmitters, peptides, lipids, nucleic acids, sugars, carbohydrates, glycoproteins, lectins, bacteria, viruses, replication inhibitors, proteases, antibiotics, antifungals, bacteriostatic compounds, toxins, microbials, anti-microbials, growth factors, angiogenic factors, nutrients, and vitamins.

In its broadest respects, the present invention is a method of grafting materials onto surfaces using infrared radiation, microwave radiation, or high voltage polymerization to modify the surface properties of the surfaces. It is to be understood that the present invention can be used to make surfaces more hydrophilic, hydrophobic or biofunctional.

An important aspect of the present invention is the micrograft initiator. The term "micrograft initiator" as used in the present invention indicates a solution that causes a desired composition to be substantially irreversibly grafted onto and into the surface of an object when exposed to infrared radiation, microwave radiation, or to high voltage polymerization as in a glow discharge chamber. Virtually any substance that is capable of polymerizing can be used with the micrograft initiator to treat the surface of an object. Several novel micrograft initiators are disclosed in the present invention. These micrograft initiators are designed for optimal performance with exposure to microwave radiation, infrared radiation or high voltage polymerization. The micrograft initiators of the present invention may be used together with polymer solutions as described herein. For example, a high molecular weight polyaniline or a low molecular weight polyaniline may be used in conjunction with the micrograft initiators of the present invention. It is to be understood that the present invention is not limited to the use of these specific polyanilines and that other molecular weights of polyanilines and other polymers may be used in the practice of the present invention. The preparation of these polyanilines is described in Example I.

The micrograft initiators of the present invention are described in detail in the Examples. In general terms, the micrograft initiators of the present invention are comprised of solutions of polyvinyl alcohol, ethylene glycol, polyaniline in N- methyl pyrrolidinone, saturated copper perchlorate in methanol or tetrahydrofuran (THF) or isopropyl alcohol, sulfuric or hydrochloric acid, peroxide, toluenesulfonic acid in acetonitrile, carboxymethylcellulose or combinations thereof. It is to be understood that variations of the specific amounts of these solutions, the reaction conditions, and the chemicals themselves as provided in the Examples, are considered within the scope of the present invention. For example, peroxides, as used in the present invention include, but are not limited to, hydrogen peroxide and benzoyl peroxide although other peroxides may be used.

Several embodiments which may be used in the present invention are described in the following general terms. In one embodiment the micrograft initiator and a mixture of the various monomers, oligomers and/or proteins that are to be grafted are prepared. The objects to be treated are dipped in the solution with the monomers or oligomers or proteins, placed in a standard microwave oven, and the grafting is then initiated. It is to be understood that any method of coating the object can be used including, but not limited to, padding, dipping or spraying the object.

In another embodiment, surfaces are prepared with a solution of the micrograft initiator, again using a dipping technique, and the objects are then exposed to microwaves to activate the surfaces of the objects. The objects are then dipped in solutions of hydrophilic monomers, hydrophobic compounds or proteins, which also have a small amount of micrograft initiators, and are subsequently placed back in the microwave oven to continue the polymerization process.

In another embodiment of the present invention, samples to be surface-modified are dipped in a different micrograft initiator as described herein and then exposed to infrared radiation. In an additional embodiment of the present invention, samples to be surface-modified are coated with the composition of the present invention before exposure to infrared radiation. The composition may be sprayed, painted, or rolled onto the surface before application of infrared radiation. Heat lamps, other specialized lamps, or exposure to solar radiation is adequate to initiate the polymerization process. The composition and method of the present invention are easily adapted to use in manufacturing on an assembly line.

Alternatively, the initial coating with the micrograft initiator is mixed with a suitable monomer/polymer mixture and then exposed to either microwave or infrared radiation and subsequently coated with another coating for which a small amount of the micrograft initiator is added to modify the surface characteristics.

Other specific combinations of the treatments described in the following examples may be employed to increase the lubricity, hydrophilicity, hydrophobicity or biofunctionality of the treated surface.

The present invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Preparation of Micrograft Initiators 1 (MI-1) and 2 (MI-2)- Each Made with High Molecular Weight Polyaniline, and Micrograft Initiator 3- Made with High (MI-3A) or Low (MI-3B) Molecular Weight Polyaniline To produce the high molecular weight polyaniline used in several micrograft initiators of the present invention, a prepolymer solution was prepared by mixing 21 ml of distilled purified aniline with 300 ml of 1 M HCl. The prepolymer solution was then placed in a three necked flask and purged with nitrogen and cooled to 5° C. In a separate container, 12 g ammonium persulfate was dissolved in 200 ml of 1 M HCl. The container was purged with pure nitrogen. The ammonium persulfate solution was cooled to 5° C. and then added to the 3 necked flask. The mixture was cooled to 0° C. and stirred for one hour. The temperature of the solution was then raised to 8° to 10° C. for 15 minutes.

Next, the solution was cooled to 0° C. and stirred for 45 minutes. The polyaniline precipitate was then washed several times by filtration with distilled water. The polyaniline precipitate was treated with 1M potassium hydroxide for 24 hours after which it was filtered, washed again for 6 to 12 hours in distilled $H_2O$, heated, and dried in a vacuum oven for 24 hours at 50° C. The dried polyaniline was ground into a powder. The mixture was optionally extracted with a soxhlet extraction with acetonitrile for 3 hours until the extract was no longer colored. This extraction produced a polyaniline powder. The polyaniline was dried in an oven at 50° C. for 6 to 7 hours and then ground to a powder. It was then treated with 1M KOH for 24 hours after which it was filtered, washed again for 6 to 12 hours in distilled $H_2O$ and dried in a vacuum oven for 24 hours at 50° C. The polyaniline precipitate was then dissolved in a N-methyl pyrrolidinone (NMP) to saturation. It is to be understood that pyrrolidinone and pyrrolidone are synonymous as used throughout the present application.

The low molecular weight polyaniline used in the micrograft initiators was made using the same protocol as for high molecular weight polyaniline with the exception of the synthesis time. In the preparation of low molecular weight polyaniline, after addition of the ammonium persulfate solution to the 3 neck flask, the mixture was cooled to 0° C. and stirred for 20 minutes. The other procedural steps were identical. These high and low molecular weight polyanilines were used in several of the micrograft initiators of the present invention and are designated with the letters A and B, respectively.

Micrograft initiator 1 (MI-1) was prepared by the following method. First 20 ml of purified poly(vinyl) alcohol (PVA) was dissolved in 60 ml $H_2O$. Ethylene glycol was added in a ratio of 50:50 vol%. Next 10 ml of a saturated solution of polyaniline in NMP was added. Ten ml of a saturated copper perchlorate solution in methanol was added. Concentrated sulfuric acid (10–25 ml) was slowly added while stirring on an ice bath followed by addition of 40 ml $H_2O_2$ (30%). The solution was purged with $N_2$ for 1 hour. This solution is micrograft initiator 1.

Micrograft initiator 2 (MI-2) was made by mixing 60 ml polyvinyl alcohol, 6 ml ethylene glycol, 11 ml of the polyaniline/N methyl pyrrolidinone (saturated solution), 4 ml of a saturated solution of copper perchlorate in THF, 25 ml concentrated sulfuric acid and peroxide. These chemicals were added using the same procedure as for MI-1.

Micrograft initiator 3 (MI-3) was made according to the same method as described above but with the following quantities: 80 ml PVA (10% vol/vol in $H_2O$); 20 ml polyaniline/NMP solution (3 ml of NMP and 0.7 g polyaniline, stirred and then added to 40 ml NMP); 25 ml concentrated sulfuric acid; 8 ml ethylene glycol; 6 ml of saturated copper perchlorate in THF; 50% by volume of $H_2O_2$ (30% wt/vol). If high molecular weight polyaniline is used in formation of MI-3, the resulting micrograft initiator is designated MI-3A. If low molecular weight polyaniline is used, the resulting micrograft initiator is designated MI-3B.

EXAMPLE 2

Preparation of a Surface Modified Stainless Steel Stent

Four ml of purified hydroxyethyl methacrylate (HEMA) was added to 4 ml of the micrograft initiator MI-1 (see Example 1). To graft poly HEMA onto the stainless steel surface, the steel was coated with this solution and then placed in an MK Industries, Inc. (Tucker, Ga.) glow discharge chamber at 2500 volts in argon gas for 2 seconds. The contact angle for a drop of water applied to the HEMA modified surface was approximately 10° C. compared to 60° C. before modification.

EXAMPLE 3

Surface Modification of Stainless Steel Slabs

To about 9 ml of MI-1 of Example 1 was added 2.5 ml of purified HEMA followed by 1 ml of THF while stirring vigorously. Next, about 2 ml to 5 ml of concentrated sulfuric acid was added. 1 $cm^2$ slabs were dipped in this solution for 5 seconds and then placed in a home microwave oven (2.5 GHz, 800 watts) for 5 seconds. Samples were removed and washed by sonication in distilled water.

EXAMPLE 4

Surface Modification of Non-Woven Polypropylene

MI-3A was used with composition 1 for surface modification of non-woven polypropylene.

Composition 1 was made by mixing 10 ml of PVA and 10 ml of $H_2O_2$ (30%) followed by 10%–50% (vol%) purified acrylic acid.

Pieces of nonwoven polypropylene (3 $cm^2$) were cleaned by sonication in distilled water and then soaked in acetone or isopropanol. The pieces were soaked in Composition 1 for 5 minutes and then soaked in MI-3A solution for 5 minutes. Pieces were then removed from MI-3A solution, placed in the microwave oven and exposed to microwaves for 30–60 seconds, removed and further soaked in Composition 1 for 5 minutes. Samples were rinsed in distilled water, followed by a distilled water rinse in a sonicator. The samples were dried and tested.

The above modified polypropylene samples were tested for contact angle shortly after modification. Contact angles measured were less than 5°. Samples were then placed in closed beakers and a 40% potassium hydroxide solution in water was added. The samples were immersed in the potassium hydroxide solution which was heated at 70° C. for 7 days. Samples were subsequently removed, washed and contact angles measured. The measured contact angles were the same as before the tests, and less than 5°. The samples were also as wettable as before the tests.

EXAMPLE 5

Surface Modification of Stainless Steel Slabs with Heparin

To 3 ml of MI-2 of Example 1 was added 10 ml of purified HEMA and 1 ml of purified THF. Concentrated sulfuric acid (7 ml) was slowly added to this solution on an ice bath followed by addition of 1 ml of THF. Heparin (10% in distilled water) was then added to this solution at 20 vol%. Next, slabs were dipped in this solution for 10 seconds, coated, placed in the microwave oven for 5 seconds, removed and washed with distilled water.

EXAMPLE 6

Cell Adhesion Tests of Surface Modified Stainless Steel Slabs

Samples of 1 $cm^2$ slabs of standard 316L stainless steel were prepared and polished using a high-speed polishing wheel until no noticeable grooves were seen using an optical microscope. Samples were then washed by sonication with 1,1,1 trichloroethane, and then by sonication in methanol, and allowed to air dry. Potassium salt solutions (0.1–1M) of 3 sulfopropylacrylate, vinylpyrrolidinone, and hydroxyethylmethacrylates, all obtained from Aldrich, were prepared using distilled water. Heparin and bovine serum albumin (BSA) solutions of 20% and 5%, respectively, were made using modified Dulbecco's minimal essential medium. Chick embryo corneal epithelial cells and liver epithelial cells were used to study cell adhesions, and the air bubble technique was used for contact angles to study the extent of hydrophilicity of the samples as described in Examples 3 and 5.

EXAMPLE 7
Contact Angle Analysis of Uncoated Stainless Steel and Surface Modified Stainless Steel Coated with Heparin or Albumin Contact angles were measured on the surface of the stainless steel slabs of Example 6 using the air bubble technique in water. Due to the small size of the contact angles, a laser beam was used and deflections off the laser beam were measured to calculate contact angles of the air bubbles with the stainless steel. These measurements are summarized in Table I and demonstrate significant reduction in the contact angle following grafting of materials onto the surface of the stainless steel.

TABLE 1

| Material Grafted | Contact Angle, degrees |
| --- | --- |
| SS Unmodified | 62 |
| PVP Modified | 4 |
| HEMA/Alb/Copolymer | 5 |
| HEMA/Albumin | 8 |
| HEMA/Heparin | 8 |

EXAMPLE 8
Cell Adhesion Analysis of Uncoated Stainless Steel and Surface Modified Stainless Steel Coated with Heparin or Albumin The modified and unmodified stainless steel slabs of Example 6 were incubated with two epithelial cell lines, corneal cells and liver cells, for various periods as shown in Table 2. Cells were seeded in a solution comprised of 10% BSA and 90% DMEM medium. Slabs were then incubated in this solution at 37° C. for various time intervals. The surfaces of the slabs were photographed through a photomicroscope and the degree of cell adhesion was determined by counting the number of cells per grid area.

The results of these tests are shown in Table 2, and indicate significant reduction in cell adhesion and spreading on the treated surfaces.

TABLE 2

| Materials Grafted | Two Hour Incubation | Eight Hour Incubation |
| --- | --- | --- |
| SS Unmodified | Significant adhesion & spreading | Significant adhesion & spreading |
| PVP | 2 cells/mm² | 5 cells/mm² |
| HEMA/Copolymer | Virtually no cells | 10 cell/cm² |
| HEMA/Heparin | 13/cm² | 150/cm² |
| HEMA/Alb/Copolymer | Virtually no cells & no spreading | Virtually no cells & no spreading |

*Four independent, modified and unmodified slabs were used, and averages were taken over these sets of samples.
Alb is bovine serum albumin,
SS is stainless steel.

These test data in the preceding Examples demonstrate significant surface enhancement for the materials tested. Small contact angles, comparable to, or in some cases, even better than the surface enhancement produced by the gamma ray process were achieved. The in vitro adhesion tests demonstrate substantial reductions in the spread of epithelial cell lines and in the degree of cellular adhesion to modified surfaces.

EXAMPLE 9
Preparation of Surface Modified Polystyrenes

The same micrograft initiator, MI-1, as described in Example 3 was used with stainless steel slabs, except that N-vinyl pyrrolidinone was employed instead of HEMA.

EXAMPLE 10
Preparation of Surface Modified Polyethylenes

The same procedure was followed as in Example 3 above except N-vinyl pyrrolidinone was employed instead of HEMA.

EXAMPLE 11
Preparation of Surface Modified Polymethylmethacrylates

The same procedure was followed as in Example 3 above except N-vinyl pyrrolidinone was employed instead of HEMA.

EXAMPLE 12
Surface Modification of Latex and Silicone Catheters

Catheters made from latex or silicone were modified according to the following procedure.

In this example, two compositions were used:

Composition 1: To about 139 ml of MI-3 without $H_2O_2$ was added 5 ml phenol. Next, about 144 ml of $H_2O_2$ (30%) was added to this solution in a final ratio of 50:50 vol% and stirred for 1 hour.

Composition 2: To 10 ml of PVA, 10 ml of $H_2O_2$ (30%) was added to achieve a 50:50 vol % ratio. Next, acrylic acid, N-vinyl pyrrolidinone or HEMA was added to achieve a final ratio v/v of 50% of acrylic acid (99% solution), purified N-vinyl pyrrolidinone or purified HEMA to the PVA/hydrogen peroxide solution. The latex or silicone catheters were soaked in composition 2 for 5 min, then in composition 1 for 5 min, followed by exposure to microwaves in an oven for about 60 seconds. Next the latex or silicone catheters were soaked in composition 2 for about 5 min.

EXAMPLE 13
Surface Modification of Nonwoven Polypropylene Material

First, a PVA/surfactant solution was made by saturating a 10% (vol/vol) PVA solution with dodecyl benzene sulfonic acid sodium salt. MI-3A solution and another composition were used.

Composition 1: To 10 ml of MI-3A was added 10 ml of acrylic acid (99% solution).

The polypropylene material was dipped in PVA/surfactant solution. About 2 ml of Composition 1 was pipetted over the sample followed by exposure to microwaves for 11 seconds in a microwave oven. The sample was rinsed with distilled water.

EXAMPLE 14
Hydrophilic Surface Modification of Stainless Steel Slabs Initiated With Infrared Radiation About 8 to 10 ml of NVP was added to each 1 ml of MI-3A solution. The stainless steel samples were immersed in this solution and exposed to infrared radiation from a tungsten light for 10 seconds. The samples were rinsed with distilled water and permitted to dry.

The sample displayed excellent hydrophilic properties.

EXAMPLE 15
Hydrophilic Surface Modification of Stainless Steel Slabs and Silicone About 40 ml of distilled acrylic acid is added dropwise to 40 ml of MI-3A of Example 1. To this solution was optionally added 5%–15% by volume poly(ethylene glycol-400) dimethacrylate (Aldrich). Other cross-linkers may be used instead of poly(ethylene glycol-400) dimethacrylate. The stainless steel slabs or silicone samples were immersed in the solution and placed in a microwave oven at low power for 10 seconds. The stainless steel slabs or silicone samples may be recoated and microwaved several times to increase the thickness of the coating.

EXAMPLE 16
Hydrophilic Surface Modification of Stainless Steel Slabs and Silicone The same method is employed as in Example 15 except that N-vinyl pyrrolidinone is used instead of acrylic acid. The samples are microwaved to graft the polymers to the surface.

EXAMPLE 17
Surface Modification of Stainless Steel Slabs and Silicone

Water may be added to the solutions of Examples 15 or 16 at 0 to 50% (vol%) to produce gel effects and was cured using an infrared micrograft initiator and infrared radiation.

EXAMPLE 18
Gel Formation Using Infrared Radiation

N-vinyl pyrrolidinone (6 ml), 1.5 ml–3.0 ml acrylic acid or methacrylic acid were added to about 1.2 ml to 2.0 ml of the solution of Example 15. Next, 1 ml of poly(ethylene glycol-400) dimethacrylate was added. After immersion in this solution, samples were exposed to low infrared radiation from a tungsten lamp source and the reaction was immediately initiated. From 1 ml to 5 ml of water was optionally added to form gels. Optionally, to increase the lubricity of the surface of the sample, phosphatidylcholine (Sigma, St. Louis) in chloroform (1% to 5% by weight) can be added to the sample before grafting. The preferable concentration of the phosphatidylcholine solution in the final solution is between approximately 0.1 to 15% by volume. Samples are placed in solution before exposure to infrared radiation which results in surface modification.

EXAMPLE 19

Infrared and heat-treated stainless steel samples were microwave treated as in Example 15. Cylink HPC-75 melamine resin (a mixture of isomers of hexa(hydroxypropylcarbamylmethyl)melamine is diluted with isopropyl alcohol in a 1:2 vol:vol ratio. Samples were then dipped in this solution and the excess removed. The samples were cured under a heating lamp for 25 minutes. Next, the samples were coated with diluted ethyl hydroxyethyl cellulose 0.1% by weight in water and allowed to cure for 20 minutes under the same infrared conditions using micrograft initiator 4 (MI-4) of Example 22. The surfaces of the samples were extremely lubricious and hydrophilic.

EXAMPLE 20

The same methods and materials were employed as in Example 19 except that from 1%–15% (by volume) micrograft initiator (MI-4) was combined with NVP as in Example 18 and separately added to HPC-75 and BERMOCOLL EBS 411 FQ (ethyl hydroxyethyl cellulose—EHEC, purchased from AKZO, Stenungsund, Sweden) (1% to 25% by volume). The resulting reaction was more rapidly initiated and completed.

EXAMPLE 21

HPC-75 was diluted with NVP, acrylic acid or methacrylic acid by 10%–50% (vol%). To this solution was added 1%–5% (vol%) of poly(ethylene glycol-400) dimethacrylate. Samples of stainless steel were then dipped and exposed to infrared radiation for 2 minutes.

Another composition employed was 0.1% to 0.5% BERMOCOLL in NVP, acrylic acid or methacrylic acid and 1%–5% by volume acrylic acid micrograft initiator as in Example 19. Samples of stainless steel were then dipped and exposed to infrared radiation for 1 minute.

To these compositions, NVP (1 to 10% vol%) was optionally added to accelerate the reaction. In addition, the initiator of Example 20 can optionally be used instead of the acrylic acid micrograft initiator.

Samples treated with the methods of this example were extremely lubricious and hydrophilic and the surface modification was completed in a very rapid manner.

EXAMPLE 22
Micrograft Initiator 4 (MI-4) Useful for Infrared Radiation

To 80 ml of PVA (10% vol:vol), 20 ml of high molecular weight polyaniline/NMP (See Example I), 20 ml of copper perchlorate saturated in isopropyl alcohol were added. To that solution were added 5 ml of concentrated HCl and 100 ml of $H_2O_2$ (30%). This initiator (MI-4) can be used in any formulation requiring an infrared micrograft initiator.

EXAMPLE 23
Preparation of Stainless Steel Slabs for Increased Lubricity

Stainless steel slabs were prepared by polishing with sandpaper, and then cleaning with the following procedure. The first cleaning cycle was a 5 minute sonication in heptane. Next, stainless steel slabs were sonicated for 5 minutes in acetone followed by an additional 5 minute sonication in isopropyl alcohol. The samples were then permitted to air dry.

A solution of CYLINK™ HPC-75 melamine resin (a mixture of isomers of hexa(hydroxypropylcarbamylmethyl) melamine) in methanol was prepared by making a 1:2 to 1:10 solution, preferably a 1:4 solution by weight, of CYLINK™ in methanol (70% to 100% distilled methanol, preferably 100% distilled). The stainless steel slabs were coated with this solution applied with a sponge. The slabs were cured in an oven at a temperature between 150° C. and 200° C., preferably 180° C., for a period of approximately 8 minutes to 30 minutes, preferably 30 minutes. The slabs were removed from the oven and permitted to cool to room temperature. The slabs were dip-coated in a solution of BERMOCOLL (EHEC) ranging from approximately 0.3% to 1.2%, preferably 0.7%. The stainless steel slabs were then cured in an oven as described above, removed from the oven, and permitted to cool to room temperature. These samples demonstrated improved wetability and lubricity compared to samples which were not treated in this manner.

EXAMPLE 24
Preparation of Silicone Samples for Increased Lubricity

Silicone samples were first cleaned by exposing the samples to an aqueous soap solution comprising any surfactant for a period of 5 minutes in a sonicator. Samples were sonicated for an additional 5 minutes in distilled water followed by further sonication for 5 minutes in ethanol. The samples were permitted to air dry.

Samples were then completely immersed in a solution of 0.3% to 1.2% of BERMOCOLL™ in distilled water. A preferred concentration of BERMOCOLL™ was 0.7% in distilled water. Excess BERMOCOLL™ solution was then permitted to drip off the silicone samples. The samples were cured in an oven at a temperature between 150° C. and 200° C., preferably 180° C., for a period of approximately 8 minutes to 30 minutes, preferably 30 minutes. Samples were removed from the oven and permitted to cool to room temperature. These samples demonstrated improved wetability and lubricity compared to samples which were not treated in this manner.

EXAMPLE 25
Treatment of Silicone Samples for Increased Lubricity with Exposure to a Wetting Agent The silicone samples were cleaned and air dried as described in Example 24. Next a solution of a silicone wetting agent Q2-5211 (Dow Corning) was prepared by mixing approximately 0.5 ml to 2 ml of Q2-5211 in 30 ml of distilled water. Preferably 1 ml of Q2-5211 was added to 30 ml of distilled water. The silicone samples were coated in this solution followed by immersion in 0.3% to 1.2% BERMOCOLL™ and distilled water. A preferred concentration of the BERMOCOLL™ solution was 0.7%. The excess BERMOCOLL™ solution was permitted to drip off the silicone samples after which the samples were cured in an oven at a temperature between about 150° C. to 200° C., preferably 180° C., for a period of approximately 8 minutes to 30 minutes, preferably 30 minutes. The samples were withdrawn from the oven and permitted to cool to room temperature. These samples demonstrated improved wetability and lubricity compared to samples which were not treated in this manner.

In another method of preparing silicone samples, silicone samples were cleaned as described above, air dried, and immersed in a solution consisting of approximately 5 ml of Q2-5211 wetting agent (Dow Corning) dissolved in 25 ml of 0.7% BERMOCOLL™ solution in distilled water. The excess solution was permitted to drip off the samples. The samples were cured in an oven at a temperature between 150° C. and 200° C., preferably 180° C., for a period of approximately 8 minutes to 30 minutes, preferably 30 minutes. Samples were removed from the oven and permitted to cool to room temperature. These samples demonstrated improved wetability and lubricity compared to samples which were not treated in this manner. Latex catheters were also treated with the method of this example and displayed excellent wetability, lubricity, and hydrophilic properties.

EXAMPLE 26
Combination of Surface Modification of Stainless Steel Slabs and Silicone Samples for Increased Lubricity with Microwave Treatment and Exposure to Wetting Agents Stainless steel slabs were polished with sandpaper and cleaned by sonication in heptane, acetone and isopropyl alcohol as described in Example 23. Silicone samples were cleaned by sonication and soap solution, water and ethanol as described in Example 24. The stainless steel slabs and silicone samples were then permitted to air dry. Next, the slabs and samples were treated as in Example 15. About 40 ml of freshly distilled acrylic acid was added dropwise to 40 ml of MI-3A of Example 1. To this solution was optionally added poly(ethylene glycol-400) dimethacrylate (Aldrich) at 5%–15% (vol%). Other cross-linkers may be used instead of poly(ethylene glycol-400) dimethacrylate. The stainless steel slabs or silicone samples were immersed in the solution and placed in a microwave oven at low power for 10 seconds. The stainless steel slabs or silicone samples may be recoated and microwaved several times to increase the thickness of the coating.

Following microwave treatment of stainless steel slabs and silicone samples, these samples were then treated with the solution of CYLINK™ in methanol and exposed to the same steps that follow the cleaning steps as described in Examples 23, 24, or 25. The samples are not subjected to these cleaning steps after exposure to microwaves. Samples treated in this manner displayed improved lubricity, wetability, and hydrophilicity, and the surface modification was accomplished rapidly. Latex catheters were also treated with the method of this example and displayed excellent wetability, lubricity, and hydrophilic properties.

EXAMPLE 27
Surface Modification of Stainless Steel Slabs and Silicone Samples with Heparin, Bovine Serum Albumin, Ampicillin or Kanamycin This example presents a method which employs infrared radiation to graft biological molecules into lubricious or hydrophilic surfaces. The biological molecules grafted were either heparin, bovine serum albumin (BSA), ampicillin or kanamycin. Heparin was then added (10% in distilled water) to the modified infrared solution described below at 20 vol%. Bovine serum albumin (BSA) was added (10% to 20% in distilled water) to the modified infrared solution described below at 5 vol%. Ampicillin (sodium salt, Sigma, St. Louis, Mo.) (10 mg/ml of distilled water) was added to the modified infrared solution described below at 1% to 5% (vol%). Kanamycin monosulfate (Sigma, St. Louis, Mo.) (10 mg/ml of distilled water) was added to the modified infrared solution described below at 1% to 5 % (by volume). Next the stainless steel slabs or silicone samples were treated as described in Examples 23, 24, 25, or 26. The modified infrared solution mentioned above uses the same solution as described in Example 14 with the following compositions and modifications Micrograft Initiator 5 (Ml-5): MI-5 was prepared on ice at approximately 4° C. to 5C. To 80 ml of PVA solution, 20 ml of polyaniline in NMP solution as in Example 1 was added and stirred. Concentrated hydrochloric acid (6 ml) was added dropwise. Ethylene glycol (8 ml) was added thereafter with 6 ml of 1 M copper perchlorate in THF. Next, about 139 ml of $H_2O_2$ (30%) was added at a final ratio of 1:1 based on volume to this solution, and stirred for 1 hour.

About 8 ml to 10 ml of NVP was added to each 1 ml of MI-5, followed by addition of either heparin, BSA, ampicillin or kanamycin as described above. The stainless steel slabs or silicone samples were immersed in this solution and exposed to infrared radiation from a heat lamp for 10 seconds. The samples were rinsed with distilled water and permitted to dry.

The sample displayed excellent wetability, lubricity, and hydrophilic properties. Latex catheters were also treated with the method of this example and displayed excellent wetability, lubricity, and hydrophilic properties.

EXAMPLE 28
Solutions used in Examples 29, 30, 31, 32, 33 and 34
A. CYLINK® HPC-75 Melamine Resin (abbreviated as Cy)

The CYLINK® HPC resin, hereinafter abbreviated Cy was a 75% aqueous solution of CYLINK® HPC resin in water.
B. SNOWTEX (Si)

This was a 20% aqueous solution of colloidal silica.
C. Carboxymethylcellulose (CMC) Sodium Salt [9004-32-4] Stock Solutions Three aqueous solutions of CMC were employed.
1. A 0.25% solution was made by mixing 0.25 g CMC in 100 g $H_2O$.
2. A 0.5% solution was made by mixing 0.5 g CMC in 100 g $H_2O$.
3. A dilute CMC solution (0.05%) was made by making a 1:10 dilution of solution C2 in $H_2O$.
D. Solutions of Aqueous CMC, Aqueous Snowtex and CYLINK® in Methanol
1. About 5 g of a 0.25% CMC in $H_2O$, 0.5 g of a 2% solution of Snowtex in $H_2O$, and 0.25 g of CYLINK® in methanol (1:4) were thoroughly mixed.
2. About 5 g of a 0.05% CMC in $H_2O$, 0.5 g of a 2% solution of Snowtex in $H_2O$, and 0.25 g of CYLINK® in methanol (1:16) were thoroughly mixed.

E. Cy:MeOH (1:4)

This was a solution of CYLINK® in methanol mixed in a ratio of 1 part CYLINK® to 4 parts methanol.

F. Cy:MeOH (1:8)

This was a solution of CYLINK® in methanol mixed in a ratio of 1 part CYLINK® to 8 parts methanol.

G. Si w/SWA (2% in $H_2O$)

This is a solution of 10 g Snowtex, 90 g $H_2O$ and 0.25 g Superwetting agent (SWA- Dow Corning).

H. Si w/SWA (1% in $H_2O$)

This is a solution of 5 g Snowtex, 95 g $H_2O$ and 0.25 g Superwetting agent (SWA- Dow Corning).

I. Micrograft Initiator 3B (MI-3B)

This micrograft initiator was made by mixing the following reagents:

a. 20 ml PA (polyaniline) low molecular weight)/NMP(N methylpyrrolidinone) [0.7g PA in 43 ml NMP];

b. 80 ml PVA (polyvinylalcohol) solution [10% vol:vol PVA in $H_2O$];

c. 25 ml concentrated $H_2SO_4$;

d. 8 ml ethylene glycol;

e. 6 ml of a saturated solution of $CuClO_4$/THF (tetrahydrofuran); and f. 139 ml $H_2O_2$ (30%)

J. Micrograft Initiator 3B (MI-3B) with acrylic acid (aa)

This solution was made by slowly adding distilled acrylic acid to MI-3B described in solution I above in equal amounts.

K. 20% [50% MI-3B: 50% acrylic acid] in Cy:MeOH (1:4)

This solution was made by mixing 2 g of MI-3B with acrylic acid (aa) from solution J above with 10 g of solution E.

L. 1% BSA in Solution D (aqueous CMC, aqueous Snowtex nd CYLINK® in methanol)

1.1% by weight of (10% BSA) in solution D1

2.1% by weight of (10% BSA) in solution D2

M. 5% BSA in Solution D (aqueous CMC, aqueous Snowtex and CYLINK® in methanol)

1.5% by weight of (10% BSA) in solution D1

2.5% by weight of (10% BSA) in solution D2

N. 90% Si w/SWA (2% in $H_2O$) 10% Cy:MeOH (1:4)

9 g Si w/SWA (2% in $H_2O$) from solution G above were mixed with 1 g Cy:MeOH (1:4) from solution E above.

0.1% toluidine blue

A solution of 1% toluidine blue was made by mixing 1 g toluidine blue with 100 g $H_2O$.

P.25% glutaraldehyde in $H_2O$

EXAMPLE 29

Surface Modification of Stainless Steel Using the Microwave Method

In the table below, the letters indicate the solutions described in Example 28. In the Rinse/Cure column below, samples were rinsed in the indicated solution, dipped in the same solution, and then cured as shown. In the Notes column below, lub. indicates lubricious. Seconds are abbreviated as "s".

TABLE 3

| Sample | 1° Coating (Solution and duration of μwave exposure) | Rinse Cure | 2° Coating (oven cure 30 min; 200° C.) | 3° Coating (oven cure 20 min; 200° C.) | Notes |
| --- | --- | --- | --- | --- | --- |
| 1* | K for 20 seconds | E | E | D1 | Not as good |
| 2* | K for 20 seconds | E | G | M1 | Not as good |
| 3* | K for 20 seconds | E | N | L1 | Not as good |
| 4* | K for 20 seconds | E | E | dip in P, then L1 | Good |
| 1,1 | K for 20 seconds | E | E | D1 | Not as good, not lub. |
| 1,2 | K for 20 seconds | E | E | m1 | Good |
| 1,3 | K for 20 seconds | E | E | L1 | Better, not lub. |
| 1,4 | K for 20 seconds | E | E | dip in P, then L1 | Good, not lub. |
| 1,5 | K for 20 seconds | E | E | μwave 10s in K, then coat with D1 | Good, very lub. |
| 2,1 | K for 20 seconds | G | G | D1 | OK |
| 2,2 | K for 20 seconds | G | G | M1 | Good, very lub. |
| 2,3 | K for 20 seconds | G | G | L1 | Not as good |
| 2,4 | K for 20 seconds | G | G | dip in P, then L1 | OK |
| 2,5 | K for 20 seconds | G | G | μwave 10s in K, then coat with L1 | Not as good |
| 3,1 | K for 20 seconds | E | N | D1 | Not as good |
| 3,2 | K for 20 seconds | E | N | M1 | Not uniform |
| 3,3 | K for 20 seconds | E | N | L1 | Not as good |
| 3,4 | K for 20 seconds | E | N | dip in P, then L1 | Not uniform |
| 3,5 | K for 20 seconds | E | N | μwave 10s in K, then coat with D1 | Not as good |
| 4,1 | K for 20 seconds | E | D | D1 | Not as good |
| 4,2 | K for 20 seconds | E | D | M1 | Not as good |
| 4,3 | K for 20 seconds | E | D | L1 | Not as good |
| 4,4 | K for 20 seconds | E | D | dip in P, then L1 | Not as good |
| 4,5 | K for 20 seconds | E | D | μwave 10s in K, then coat with D1 | Not as good |
| A1(1,2) | K for 20 seconds | E | E | M2 | Very Good |
| A2(1,3) | K for 20 seconds | E | E | L2 | Very Good |
| A3(1,4) | K for 20 seconds | E | E | dip in P, then L2 | Very Good |
| A4(1,5) | K for 20 seconds | E | E | μwave 10s in K, the D2 | Very Good |
| A5(4*) | K for 20 seconds | E | E | dip in P, then L2 | Very Good |
| A5'(4*) | K for 20 seconds | E | G | dip in P, then L2 | Very Good |
| B1(2,2) | K for 20 seconds | G | G | M2 | Very Good |
| B2(2,4) | K for 20 seconds | G | G | dip in P, then L2 | Very Good |
| C(3,3) | K for 20 seconds | E | N | L2 | Very Good |
| D(4,1) | K for 20 seconds | D2 | D2 | D2 | Very Good |

TABLE 3-continued

| Sample | 1° Coating (Solution and duration of μwave exposure) | Rinse Cure | 2° Coating (oven cure 30 min; 200° C.) | 3° Coating (oven cure 20 min; 200° C.) | Notes |
|---|---|---|---|---|---|
| E | K for 20 seconds | F | H | | Very Good |
| F | K for 20 seconds | F | L | | Very Good |

EXAMPLE 30

BSA Treatment of Selected Samples from Example 29

Samples listed in Table 4 were first treated as shown in Example 29 before the BSA treatments as indicated in Table 4. In the table below, the letters in the procedure column indicate the solutions described in Example 28. IR indicates exposure to infrared radiation for the time indicated.

TABLE 4

| Sample from Ex. 29 | Procedure | Cure |
|---|---|---|
| A1 | prep sample (as in Ex. 29), soak in P 1 min, mix 5 ml 2% BSA in H₂O + 0.5 ml 2% glut., coat sample with mixture | IR for 45 min |
| A2 | prep sample (as in Ex. 29), soak in P 1 min, mix 5 ml 2% BSA in H₂O + 0.5 ml 2% glut., coat sample with mixture | " |
| A3 | prep sample (as in Ex. 29), soak in P 1 min, mix 5 ml 2% BSA in H₂O + 0.5 ml 2% glut., coat sample with mixture | " |
| A4 | prep sample (as in Ex. 29), soak in P 1 min, mix 5 ml 2% BSA in H₂O + 0.5 ml 2% glut., coat sample with mixture | " |
| A5 | prep sample (as in Ex. 29), soak inP 1 min, mix 5 ml 2% BSA in H₂O + 0.5 ml 2% glut., coat sample with mixture | " |
| A5' | prep sample (as in Ex. 29), soak in P 1 min, mix 5 ml 2% BSA in H₂O + 0.5 ml 2% glut., coat sample with mixture | " |
| B1 | prep sample (as in Ex. 29), soak in P 1 min, mix 5 ml 2% BSA in H₂O + 0.5 ml 2% glut., coat sample with mixture | " |
| B2 | prep sample (as in Ex. 29), soak in P 1 min, mix 5 ml 2% BSA in H₂O + 0.5 ml 2% glut., coat sample with mixture | " |
| C | prep sample (as in Ex. 29), soak in P 1 min, mix 5 ml 2% BSA in H₂O + 0.5 ml 2% glut., coat sample with mixture | " |
| D | prep sample (as in Ex. 29), soak in P 1 min, mix 5 ml 2% BSA in H₂O + 0.5 ml 2% glut., coat sample with mixture | " |
| E | prep sample, soak in solution P1 min, mix 5 ml [10% BSA:C3 + 0.5 ml 2% glut., coat sample with mixture | " |
| E | prep sample, soak in solution P1 min, mix 5 ml [10% BSA:C3 + 0.5 ml 2% glut., coat sample with mixture | oven cure 30 min 200° C. |
| F | prep sample, soak in solution P1 min, mix 5 ml [10% BSA:C3 + 0.5 ml 2% glut., coat sample with mixture | oven cure 30 min 200° C. |
| F | prep sample, soak in solution P1 min, mix 5 ml [10% BSA:C3 + 0.5 ml 2% glut., coat sample with mixture | oven cure 30 min 200° C. |

Samples A1 through F all received infrared curing and displayed good surface coating with BSA after soaking in a saline solution for 24 hours at 37° C. Excellent BSA coatings were obtained with samples D, B2, C and A3.

EXAMPLE 31

Methods of Post-Modification of Stainless Steel Samples with Heparin

Six stainless steel samples were each immersed in solution K from Example 28 and microwaved for about 20 seconds for each 3 ml of coating solution. Samples were rinsed in distilled H₂O. Next, 3 samples were coated in solution G and designated Si1, Si2, and Si3. The other 3 samples were coated in solution F and designated Cy1, Cy2, and Cy3. All samples were cured in an oven at 200° C. for 30 min.

Modification Method 1

Samples Si1 and Cy1 were coated with a solution consisting of 6 ml solution L1, 1 drop superwetting agent (SWA), and 0.25 ml of solution P, and cured in an oven for about 18 minutes at 200° C.

Modification Method 2

Samples Si2 and Cy2 were coated with a solution consisting of 6 ml 1% (10% BSA)/0.7% BERMOCOLL solution, 1 drop superwetting agent (SWA), and 0.25 ml of solution P, and cured in an oven for about 18 minutes at 200° C.

Modification Method 3

Samples Si3 and Cy3 were coated with a solution consisting of 3 ml L1; 3 ml 1% (10% BSA)/0.7% BERMOCOLL solution, 1 drop superwetting agent (SWA), and 0.25 ml of solution P, and cured in an oven for about 18 minutes at 200° C.

Heparin Post-Modification Method 1

All of these samples, Si1, Si2, Si3, Cy1, Cy2, and Cy3 were then coated with a solution consisting of 1 ml 2% BSA in H₂O, 3 ml (10% heparin sodium salt/H₂O), and 0.5 ml of 2% glutaraldehyde. Samples were then cured with infrared radiation for 45 minutes followed by soaking in saline for 72 hours at 37° C. Samples were rubbed by hand and dyed with solution O. All samples displayed uniform distribution of the toluidine blue dye and appeared dark purple in color. Rubbing the samples did not remove the coating as evidenced by the uniform distribution of the toluidine blue dye.

Two of each sample (1,2), (1,4), (2,1), (2,2), and (3,3) were treated as shown in Example 29. Two of each sample (E-oven cure), (F oven cure), and (F- infrared cure) were treated as shown in Example 30. One sample from each condition was then treated with the heparin post-modification method as described above in this example (Example 31), coated with a solution consisting of 1 ml 2% BSA in H₂O, 3 ml 10% heparin sodium salt/H₂O, and 0.5 ml of 2% glutaraldehyde followed by curing under infrared radiation for about 45 min.

A comparison of the heparin treated samples with the corresponding samples not treated with heparin revealed that the heparin-treated samples retained a dark blue-purple color when immersed in solution O (toluidine blue solution) for 20 seconds and then rinsed in $H_2O$. Samples not treated with heparin retained no dye when immersed in solution O for 20 seconds and then rinsed in $H_2O$. The presence of the intense dye color indicated the presence of heparin coating the surface.

Heparin Post-Modification Method 2

In another heparin post modification method, several stainless steel coupon samples treated as shown in Tables 3 and 4 were post-modified with heparin as follows: 1 ml (10% BSA) was mixed with 3 ml $H_2O$, 0.5 ml (10% heparin in $H_2O$) and 0.5 ml (25% glutaraldehyde). The samples were dip-coated and cured under infrared radiation for 45 minutes. After staining with toluidine blue the results showed that coupons subject to heparin post-modification retained dye while coupons without heparin post-modification did not.

A comparison of the heparin treated samples with the corresponding samples not treated with heparin revealed that the heparin-treated samples retained a dark blue-purple color when immersed in solution O (toluidine blue solution) for 20 seconds and then rinsed in $H_2O$. Samples not treated with heparin retained no dye when immersed in solution O for 20 seconds and then rinsed in $H_2O$. The presence of the intense dye color indicated the presence of heparin coating the surface.

EXAMPLE 32

Preparation of Stainless Steel Coupons for Heparin Coating

Stainless steel coupons of types 8, 9, 10, 11, 12B, and 12C were cleaned in a solution of heptane, acetone and isopropanol with sonication. Each type represents a different modification process. Samples were placed in solution K from Example 28 and microwaved for 8 periods at 5 seconds each followed by a rinse in distilled $H_2O$. Next, samples were coated with solution H and cured in an oven at 200∞ C. for 30 min. Samples were coated with 6 ml of solution D2 (5 g 0.05% CMC in $H_2O$, 0.5 g of solution H, and 0.25 g of CYLINK in methanol (1:16)) plus 0.25 ml of solution P. Samples were cured at 200° C. for 20 minutes.

The different stainless steel types were treated as shown below:

1) Type 8- Heparinized with 4 coats
   1 ml 2% BSA
   3 ml $H_2O$
   0.5 ml 2% heparin
   0.5 ml 5% glutaraldehyde
   Cured with infrared radiation for 45 minutes after each coating.
2) Type 9- Heparinized with 4 coats
   1 ml 2% BSA
   3 ml $H_2O$
   0.5 ml 2% heparin
   0.5 ml 5% glutaraldehyde
   Cured with infrared radiation for 45 minutes after each coating.
   Soak in 25% glutaraldehyde for 1 hour.
   Air dry.
3) Type 10- Heparinized with 4 coats
   1 ml 2% BSA
   3 ml $H_2O$
   0.5 ml 2% heparin
   0.5 ml 5% glutaraldehyde
   Cured with infrared radiation for 45 minutes.
4) Type 11- Heparinized with 4 coats
   1 ml 2% BSA
   3 ml $H_2O$
   0.5 ml 2% heparin
   0.25 ml 2% carbodiimide in DMSO (weight/weight)
   0.5 ml 5% glutaraldehyde
   Cured with infrared radiation for 45 minutes after each coating.
5) Type 12B- Heparinized with 2 coats
   1 ml 2% BSA
   3 ml $H_2O$
   0.5 ml 2% heparin
   0.5 ml 5% glutaraldehyde
   0.25 ml 2% carbodiimide in DMSO (weight/weight)
   Cured with infrared radiation for 45 minutes after each coating.
6) Type 12C- Heparinized with 3 coats
   1 ml 2% BSA
   3 ml $H_2O$
   0.5 ml 2% heparin
   0.5 ml 5% glutaraldehyde
   0.25 ml 2% carbodiimide in DMSO (weight/weight)
   Cured with infrared radiation for 45 min after each coating.

The samples in this Example were soaked in saline for 7 to 21 days and repeatedly rubbed, dyed and dyed again in solution O. The samples maintained their heparin coating as indicated by the intensity of the dye.

EXAMPLE 33

Surface Modification of Stainless Steel Guidewires to Increase Lubricity

Guidewires were cleaned by sonication for 10 minutes in each of the following solutions: heptane; acetone; and isopropanol. Samples were immersed in solution K and microwaved for 8 intervals of 5 seconds each. Samples were then rinsed with distilled water. Samples were soaked in solution G for 10 minutes and cured in the oven at 170° C. for 20 minutes. Next, samples were soaked in solution C1 for 20 minutes; dried at 60° C. for 10 minutes; and cured at 170° C. for 10 minutes. Samples were then soaked in solution C2 for 10 minutes; dried at 60° C. for 10 minutes; and cured at 170° C. for 10 minutes. Again, samples were soaked in solution C2 for 10 minutes; dried at 60° C. for 10 minutes; and cured at 170° C. for 10 minutes.

The lubricities of these surface modified guidewires were tested by soaking in saline at 37° C. for 30 minutes, placing them individually between polyvinyl alcohol (PVA) foam pads saturated with saline, pulling the wire from the pads and measuring the force required to remove the wire from the pads. Following 20 passes of the guidewire between the pads, there was no detectable change in the force required to remove the wire from the pads. This result indicates that the lubricious coating is stable after repeatedly pulling the wires through the PVA foam pads.

EXAMPLE 34

Surface Modification of Stainless Steel Slabs to Increase Lubricity

Stainless steel slabs were modified to increase lubricity according to the same protocol as described in Example 33 used to modify guidewires for lubricity with one exception, all three CMC layers were composed of solution C1.

The lubricities of these surface modified stainless steel slabs were tested by soaking in saline at 37° C. for 30 min, placing between PVA foam pads saturated with saline, pulling the slabs from the pads several times and measuring the force required to remove the slabs from the pads. There was no detectable change in the force required to remove the slabs from the pads. This result indicates that the lubricious coating is stable after repeatedly pulling the slabs through the PVA foam pads.

EXAMPLE 35

Surface Modification of Silicone Catheters and Slabs to Increase Lubricity

Silicone catheters and slabs were modified to increase lubricity according to the same protocol as described in Example 34 used to modify stainless steel slabs for lubricity.

The lubricities of these surface-modified silicone catheters and slabs were tested by soaking in saline at 37° C. for 30 min, placing between PVA foam pads saturated with saline, pulling the catheters and slabs from the pads several times and measuring the force required to remove the catheters and slabs from the pads. There was no detectable change in the force required to remove the catheters and slabs from the pads. This result indicates that the lubricious coating is stable after repeatedly pulling the catheters and slabs through the PVA foam pads.

EXAMPLE 36

Preparation of a Micrograft Initiator 6 (MI-6)

Micrograft initiator 6 was made in the following manner.

Solution A was made by mixing 20 ml 0.2% aqueous CMC and 3 ml low molecular weight polyaniline (PA) in NMP (0.7 g PA/43 ml NMP).

Solution B was made by mixing 2.0 g p-toluenesulfonic acid monohydrate in 10 ml acetonitrile and 1 ml distilled $H_2O$.

Solution C was made by mixing 50% (combination of the resulting solutions A and B) and 50% hydrogen peroxide (30%) on a volume:volume basis. This solution is micrograft initiator 6 (MI-6). At this point, micrograft initiator 6 may be mixed with monomers as described in the next paragraph, or any other materials such as protein desired for micrograft incorporation.

Next, solution C and monomer (for example acrylic acid or NVP although other monomers may be used) were mixed with poly(ethylene glycol-400) dimethacrylate in a ratio of 45:45:10. The resulting solution made with monomer has been used to make nonwoven polypropylene more hydrophilic.

EXAMPLE 37

Use of Micrograft Initiator 6 (MI-6) to Increase Hydrophilicity of Polypropylene Non-Woven Fabric In the following treatment, pieces of non-woven polypropylene fabric were soaked in THF at 60° C. for 30 minutes, wetted with PVA surfactant solution, and the excess surfactant solution was removed by blotting. These pieces of fabric were then treated with the following conditions (A–E) and exposed to microwaves in a microwave oven on high for 5 periods of 5 seconds each.

A. 0.1 g MI-6, 1 g acrylic acid, 9 g of NVP, and 0.2 g PEG.
B. 0.1 g MI-6, 0.2 g acrylic acid, 9.8 g NVP, and 0.1 g PEG.
C. 0.1 g MI-6, 0.2 g methacrylic acid, 9.8 g NVP, and 0.1 g PEG.
D. 0.1 g MI-6, 0.5 g methacrylic acid, 0.5 g acrylic acid, 9.0 g NVP, and 0.2 g PEG.
E. 0.1 g MI-6, 0.1 g methacrylic acid, 0.1 g acrylic acid, 9.8 g NVP, and 0.1 g PEG.

These treated pieces of polypropylene fabric were examined by placing a drop of $H_2O$ on the fabric. The drop of water was absorbed quickly indicating excellent wetability of the surface modified polypropylene.

It should be understood, of course, that the foregoing relates only to preferred embodiments of the present invention and that numerous modifications or alterations may be made therein without departing from the spirit and the scope of the present invention.

I claim:

1. A method of modifying a surface of an object, comprising:

coating the object with a micrograft initiator and a hydrophilic polymer, a hydrophobic polymer, or a biofunctional compound, or a combination of these; and, exposing the coated object to infrared radiation, microwave radiation or high voltage polymerization, thereby producing a graft to the surface.

2. The method of claim 1, wherein the object is selected from the group consisting of metals, woods, polymers, ceramics, plastics, fibers and composites thereof.

3. The method of claim 1, wherein the object is a medical device, surgical instrument or an implant.

4. The method of claim 1, wherein the object is a web.

5. The method of claim 1, wherein the surface is made from substances comprising fluorocarbon polymers, polyolefins, polyolefin/hydrocarbon polymers, polyvinyl chloride, polypropylene, polystyrene, silicone, polyacrylates, methacrylates, styrene-butadiene copolymers, ethylene propylene copolymers, styrene-ethylene/butadiene/styrene block copolymers, polycarbonates, fluorocarbon polymers, polyperfluoroethylenepropylene, polysiloxanes, polyurethanes, polyurethane polyester, polyether block copolymers, polyvinyl chloride, polyesters, polyethylene terephthalate, vinyl, or polycarbonate/polydimethylsiloxane copolymer.

6. The method of claim 1, wherein the biofunctional compound comprises a protein, receptor, enzyme, enzyme inhibitor, immunological molecule, hormone, neurotransmitter, peptide, lipid, phospholipid, nucleic acid, sugar, carbohydrate, glycoprotein, lectin, bacterium, virus, replication inhibitor, protease, antibiotic, antifungal, bacteriostatic compound, toxin, microbial, anti-microbial, growth factor, angiogenic factor, nutrient, phosphatidylcholine, anti-coagulent, or vitamin.

7. The method of claim 1, wherein the hydrophilic polymer comprises hydroxyethyl methacrylate, N-vinyl pyrrolidinone, carboxymethyl cellulose, acrylamide, polyethylene glycol, hydroxypropyl acrylamide, sulfopropyl acrylate, styrene sulfonic acid, potassium styrene sulfonic propyl acrylate, methacrylamide, acrylate, acrylic acid, methacrylic acid, hexa(hydroxypropylcarbamlymethyl) melamine, ethylhydroxyethyl cellulose, or protein.

8. The method of claim 1, wherein the hydrophobic polymer comprises polyolefin, isobutene, methacrylate, hydroxyethyl methacrylate, halogenated polymer, fluorinated polymer, or styrene polymers.

9. The method of claim 1, wherein the micrograft initiator comprises:

a first solution of polyvinyl alcohol, ethylene glycol, and polyaniline dissolved in N-methyl pyrrolidinone;

a second solution of copper perchlorate; and a third solution comprising a mixture of the second solution, the first solution, acid and peroxide.

10. The method of claim 9, wherein the second solution is copper perchlorate in methanol.

11. The method of claim 9, wherein the second solution is copper perchlorate in tetrahydrofuran.

12. The method of claim 9, wherein the second solution is copper perchlorate in isopropyl alcohol.

13. The method of claim 1, wherein the micrograft initiator comprises:
   a first solution of polyvinyl alcohol, acid, and polyaniline dissolved in N-methyl pyrrolidinone;
   a second solution of copper perchlorate in tetrahydrofuran, and ethylene glycol; and
   a third solution comprising a mixture of the second solution, the first solution, phenol and peroxide.

14. The method of claim 1, wherein the micrograft initiator comprises:
   a first solution of polyvinyl alcohol, and polyaniline dissolved in N-methyl pyrrolidinone;
   a second solution of copper perchlorate in isopropyl alcohol; and
   a third solution comprising a mixture of the second solution, the first solution, acid and peroxide.

15. The method of claim 1, wherein the micrograft initiator comprises:
   a first solution of polyvinyl alcohol, polyaniline dissolved in N-methyl pyrrolidinone, and acid;
   a second solution of copper perchlorate in isopropyl alcohol, and ethylene glycol; and
   a third solution comprising a mixture of the second solution, the first solution, and peroxide.

16. The method of claim 1, wherein the micrograft initiator comprises:
   a first solution of polyvinyl alcohol, polyaniline dissolved in N-methyl pyrrolidinone, and acid;
   a second solution of copper perchlorate in tetrahydrofuran, and ethylene glycol; and
   a third solution comprising a mixture of the second solution, the first solution, and peroxide.

17. The method of claim 1, wherein the micrograft initiator comprises:
   a first solution of aqueous carboxymethylcellulose, and polyaniline dissolved in N-methyl pyrrolidinone;
   a second solution of p-toluenesulfonic acid in acetonitrile, and water; and
   a third solution comprising a mixture of the second solution, the first solution, and peroxide.

18. A method of modifying a surface of an object, comprising:
   coating the object with (a) a micrograft initiator and (b) a hydrophilic polymer, a hydrophobic polymer, a biofunctional compound, or a combination of these; and,
   exposing the coated object to infrared radiation, microwave radiation or high voltage polymerization, thereby producing a graft to the surface, wherein the object is a medical device, surgical instrument or an implant.

19. The method of claim 18, wherein the medical device comprises a catheter, intravenous catheter, central venous catheter, stent, wire, guidewire, graft, balloon, suture, screw, staple, pin, plate, drainage device, shunt, tube, gastrointestinal tubes, enteral feeding tubes, vascular tube, vascular shunt, tube for placement in the respiratory system, endotracheal and tracheostomy tubes and cuffs, tube to drain the middle ear, wound drainage tube, fluid drainage tube, tube for placement in the urinary system, tube for placement in the reproductive system, tube for placement in the cardiovascular system, tube which act as shunts, cuff, pump, minipump, electrode, prosthetic device, artificial joint, artificial lens, laser angioplasty device, balloon angioplasty device, ventricular assist, blood dialysis components, blood oxygenators, blood bags, test tubes, blood collection tubes, vacutainers, syringes, needles, pipettes, pipette tips, blood tubing or a contact lens.

20. The method of claim 18, wherein the implant comprises an artificial knee, ankle, hip, shoulder, thyroplastic device, laryngoplastic device, artificial larynx, pump, tube, shunt, intraocular implant, lens implant, contact lens, electrode, corneal inlay, kerato-prosthesis, vascular stent, epikeratophalia device, glaucoma shunt, retinal staple, scleral buckle, dental prosthesis, dental implants, vascular graft, soft tissue prosthesis, hard tissue prosthesis, pumps, electrical devices including stimulators and recorders, auditory prosthesis, pacemaker, mammary implant, penile implant, cranio/facial tendon, artificial joint, tendon, ligament, menisci, disks, artificial bone, artificial organs including artificial pancreas, artificial heart, artificial limb or heart valve.

21. The method of claim 18, wherein the surgical instrument comprises a probe, retractor, tissue separator, vessel separator, irrigation tool, aspiration tool, phacoemulsification tool, sponge, hemostat, clamp, blade, scalpel blades, glove, lens glide, positioning tool, catheter, forceps, insertion tool, staple or suture.

22. The method of claim 18 wherein the micrograft initiator comprises:
   a first solution of polyvinyl alcohol, ethylene glycol, and polyaniline dissolved in N-methyl pyrrolidinone;
   a second solution of copper perchlorate; and
   a third solution comprising a mixture of the second solution, the first solution, acid and peroxide.

23. The method of claim 18, wherein the hydrophilic polymer comprises hydroxyethyl methacrylate, N-vinyl pyrrolidinone, carboxymethyl cellulose, acrylamide, polyethylene glycol, hydroxypropyl acrylamide, sulfopropyl acrylate, styrene sulfonic acid, potassium styrene sulfonic propyl acrylate, methacrylamide, acrylate, acrylic acid, methacrylic acid, hexa(hydroxypropylcarbamlymethyl) melamine, ethylhydroxyethyl cellulose, or protein.

24. A method of modifying a surface of an object, comprising:
   coating the object with (a) a rhicrograft initiator and (b) a hydrophilic polymer, a hydrophobic polymer, a biofunctional compound, or a combination thereof; wherein the micrograft initiator comprises (a) a first solution containing polyaniline dissolved in N-methyl pyrrolidinone, (b) a second solution containing copper, perchiorate or p-toluenesulfonic acid, and (c) a peroxide; and
   exposing the coated object to infrared radiation, microwave radiation or high voltage polymerization, thereby producing a graft to the surface.

25. The method of claim 24, wherein the object is selected from the group consisting of metals, woods, polymers, ceramics, plastics, fibers and composites thereof.

26. The method of claim 24, wherein the object is a medical device, surgical instrument or an implant.

* * * * *